United States Patent [19]

Nakayama et al.

[11] Patent Number: 5,430,195
[45] Date of Patent: Jul. 4, 1995

[54] DIAMINO COMPOUNDS AND LIQUID CRYSTAL ALIGNING FILMS

[75] Inventors: Minoru Nakayama, Minamata; Toshiya Sawai; Shizuo Murata, both of Ichihara, all of Japan

[73] Assignee: Chisso Corporation, Osaka, Japan

[21] Appl. No.: 328,463

[22] Filed: Oct. 25, 1994

Related U.S. Application Data

[62] Division of Ser. No. 141,600, Oct. 27, 1993.

[30] Foreign Application Priority Data

Oct. 29, 1992 [JP] Japan .................... 4-313995
Nov. 24, 1992 [JP] Japan .................... 4-336728

[51] Int. Cl.$^6$ ............. C07C 205/35; C07C 217/14
[52] U.S. Cl. ............. 568/586; 528/125; 528/126; 564/322; 564/430; 568/721
[58] Field of Search ............. 564/322, 430; 528/125, 528/126; 568/721, 586

[56] References Cited

FOREIGN PATENT DOCUMENTS 0389092 9/1990 European Pat. Off.

*Primary Examiner*—Peter O'Sullivan
*Attorney, Agent, or Firm*—Wenderoth, Lind & Ponack

[57] ABSTRACT

The present invention is to provide new diamino compounds useful for raw materials for production of liquid crystal aligning films that have excellent aligning properties and uniform and high pretilt angles over the whole display surface of wide substrates without afterimage phenomenons. The liquid crystal aligning films are constituted by a certain polyimide having as a principal constituent a structure unit represented by the formula;

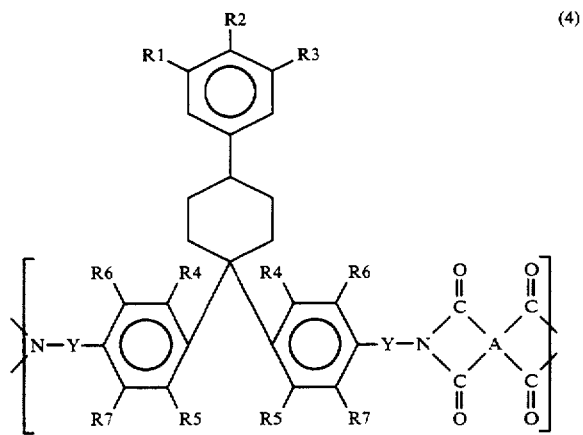

(4)

1 Claim, 3 Drawing Sheets

DIAMINO COMPOUNDS AND LIQUID CRYSTAL ALIGNING FILMS

This is a divisional application of Ser. No. 08/141,600, filed Oct. 27, 1993.

BACKGROUND OF THE INVENTION

The present invention relates to new diamino compounds and liquid crystal aligning films. More particularly, the present invention relates to new diamino compounds, and to dinitro compounds and diol compounds which are intermediates of the diamino compounds, and to liquid crystal aligning films having a high pretilt angle that is obtained by using the diamino compounds.

The main current of liquid crystal display devices which are used in conventional clocks, watches and electronic calculators is a twist nematic (abbreviated as TN hereinafter) mode having a structure in which molecular alignment of nematic liquid crystals is twisted at an angle of 90 degrees on the surface of a couple of upper and lower electrode substrates. However, when the TN mode is driven by high duty, it is insufficient to obtain improved display in quality and size because it shows an indistinct contrast and a narrow viewing angle.

Since a liquid crystal display device using super twisted birefringence effect (T. J. Scheffer and J. Nethriug, *Appl. Phys. Lett.*, 45 (10), 1021 (1984)) has been reported, a liquid crystal display device using supertwist nematic (abbreviated as STN hereinafter) mode in which the molecular alignment of nematic liquid crystals is twisted at angles of 180–300 degrees between the upper and lower electrode substrates has been developed and then large panel liquid crystal display devices having excellent display quality are developing.

It is insufficient to only align the liquid crystal molecules of aligning films used in such liquid crystal display devices. To secure good responsibility and bistability, it is necessary to have a certain angle, the so-called pretilt angle between substrate surfaces and liquid crystal molecules. It is desired to widen the pretilt angle in proportion to the twist angle. In aligning films having a relatively narrow twist angle (twisted at 180–200 degrees), it is sufficient to have pretilt angles of three degrees and below. In aligning films having a twist angle of 200–300 degrees along with better display quality, it is necessary to use the aligning films having uniform and higher pretilt angles (5 degrees $< \theta \leq 10$ degrees) covering the broad display surface of a substrate.

There are also polyimide aligning films having high pretilt angles for the STN mode. Problems of these films are uniformity and reproducibility of pretilt angles over the whole display surface of a substrate.

In order to obtain the high pretilt angles definitely, the best mode which is currently conducted is thin film formation by vacuum oblique evaporation of SiO and the like. However, as the films are mass-produced by the vacuum oblique evaporation, it is a costly process in its production unit.

When the same scene of a liquid crystal display device is lighted up for a long time, an afterimage phenomenon may be found after the scene has disappeared. It is considered that the phenomenon is due to electric double layers which are produced on the aligning film surface by ion components of impurities contained in the liquid crystal since DC components are applied on the liquid crystal display device, electric charge differences which are produced between upper and lower substrates, and electric potential differences from the stable electric charge differences. Particularly, in case of TFT devices, since DC components can not be removed for characteristics of the devices, the afterimage phenomenon is more conspicuous and serious than that of TN and STN.

Accordingly, by using a simple method employed in aligning films of usual TN modes, namely by surface treatment of rubbing organic thin film, it is desired to realize the aligning film which does not show the afterimage phenomenon, and can realize good aligning characteristics and high pretilt angles having uniformity and reproducibility.

Japanese Publication of Unexamined Patent Application No. 61-240223 discloses a liquid crystal display device that is equipped with a liquid crystal aligning films produced from a polyimide resin having a repeating unit represented by a formula:

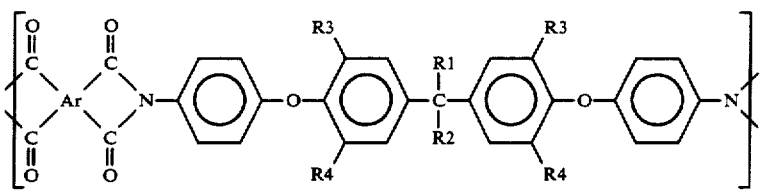

wherein R1 and R2 indicate an alkyl group having 1 to 3 carbon atoms, and R3 and R4 indicate hydrogen or an alkyl group having 1 or 2 carbon atoms, respectively.

As raw materials for the polyimide resin, an embodied example is disclosed by using a diamine represented by a formula:

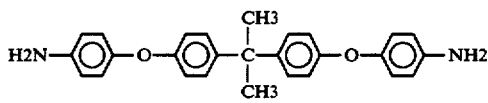

However, the polyimide aligning films produced from the above diamine have a problem that high pretilt angles are unobtainable as shown in the comparative examples described hereinafter and the afterimage phenomenon is found.

SUMMARY OF THE INVENTION

An object of the present invention is to solve the above problems and to provide liquid crystal aligning films and liquid crystal display devices which are obtained simply by rubbing treatment and have excellent aligning properties and uniform and high pretilt angles over the whole display surface of wide substrates without afterimage phenomenons, and to provide new diamino compounds useful as their raw materials, and dinitro and diol compounds which are intermediates of the above diamino compounds.

The inventors of the present invention have studied earnestly and found that liquid crystal aligning films produced from diamino compounds having a special structure unit do not show the afterimage phenomenons, and these films have excellent aligning properties and high pretilt angles which are uniform over the whole display surface of wide substrates.

The present invention have the following constitution.

1) A diamino compound represented by the general formula (I):

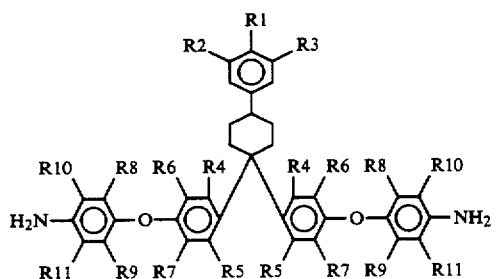

(1)

wherein R1 to R3 are hydrogen or an alkyl group having 1 to 8 carbon atoms, respectively, and a part or all of them may be the same or different. Further, R4 to R11 are hydrogen, fluorine, trifluoromethyl or an alkyl group having 1 to 3 carbon atoms, respectively, and a part or all of them may be the same or different.

2) A dinitro compound represented by the general formula (2):

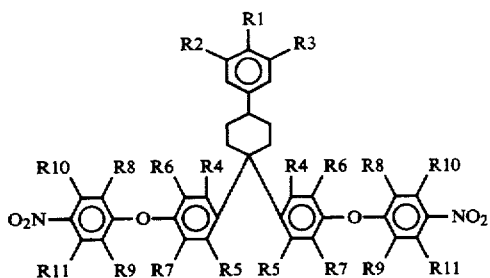

(2)

wherein R1 to R3 are hydrogen or an alkyl group having 1 to 8 carbon atoms, respectively, and a part or all of them may be the same or different. Further, R4 to R11 are hydrogen, fluorine, trifluoromethyl or an alkyl group having 1 to 3 carbon atoms, respectively, and a part or all of them may be the same or different.

3) A diol compound represented by the general formula (3):

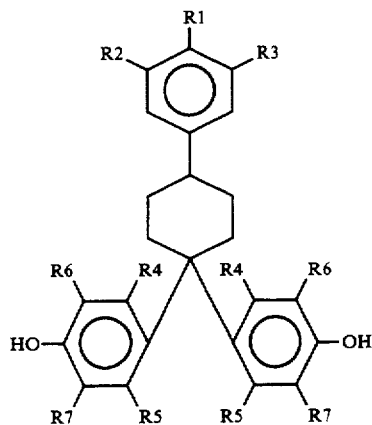

(3)

wherein R1 to R3 are hydrogen or an alkyl group having 1 to 8 carbon atoms, respectively, and a part or all of them may be the same or different. Further, R4 to R7 are hydrogen, fluorine, trifluoromethyl or an alkyl group having 1 to 3 carbon atoms, respectively, and a part or all of them may be the same or different.

4) A liquid crystal aligning film obtained by using the polyimide having as a principal constituent a structure unit represented by the general formula (4):

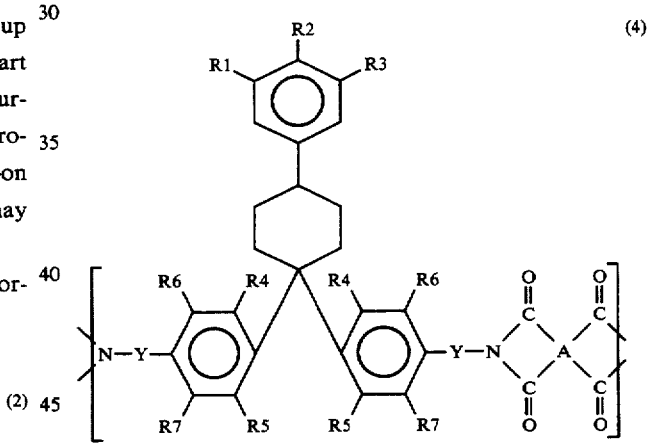

(4)

wherein R1 to R3 are hydrogen or an alkyl group having 1 to 8 carbon atoms, respectively, and a part or all of them may be the same or different,

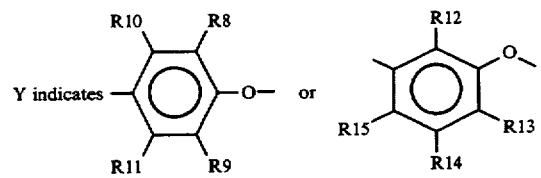

and R4 to R15 are hydrogen, fluorine, trifluoromethyl or an alkyl group having 1 to 3 carbon atoms, respectively, and a part or all of them may be the same or different, and A indicates an aliphatic or aromatic group having a valence of 4.

5) A liquid crystal aligning film obtained by using the polyimide described in 4), wherein the polyimide is obtained by reacting a tetracarboxylic dianhydride represented by the formula (5) and diamino compounds represented by the formula (1) and/or the formula (6) in a solvent to produce a polyamic acid and heating the resultant polyamic acid.

A indicates an aliphatic or aromatic group having a valence of 4.

6) A liquid crystal aligning film obtained by using the polyimide described in 4), wherein the polyimide is

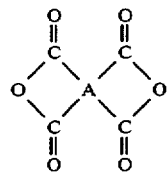
(5)

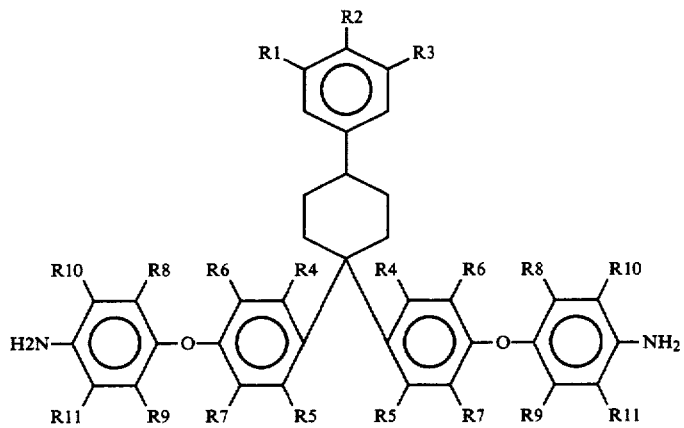
(1)

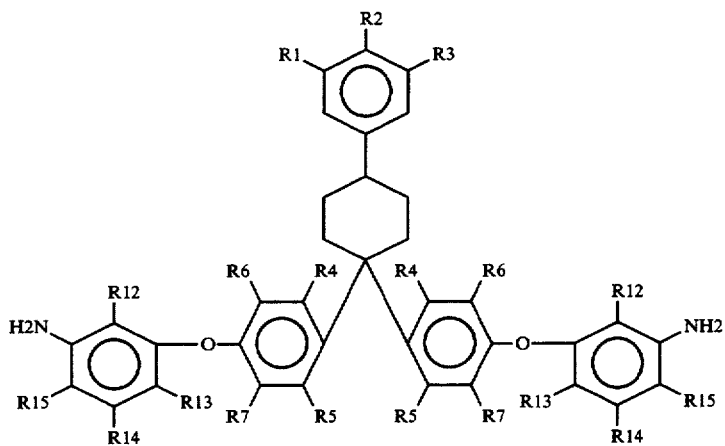
(6)

wherein R1 to R3 are hydrogen or an alkyl group having 1 to 8 carbon atoms, respectively, and a part or all of them may be the same or different, R4 to R15 are hydrogen, fluorine, trifluoromethyl or an alkyl group having 1 to 3 carbon atoms, respectively, and a part or all of them may be the same or different, and obtained by reacting a tetracarboxylic dianhydride represented by the formula (5) and diamino compounds represented by the formula (1) and/or the formula (6) and a silicon compound represented by the formula (7) in a solvent to produce a polyamic acid and heating the resultant polyamic acid.

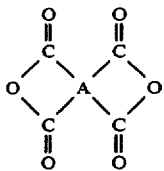
(5)

(1)

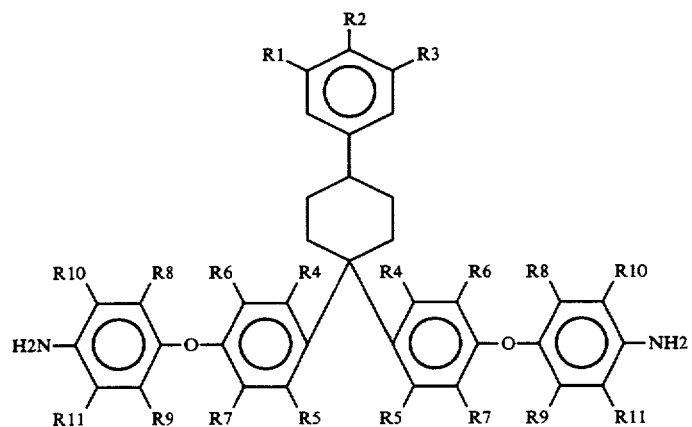

(6)

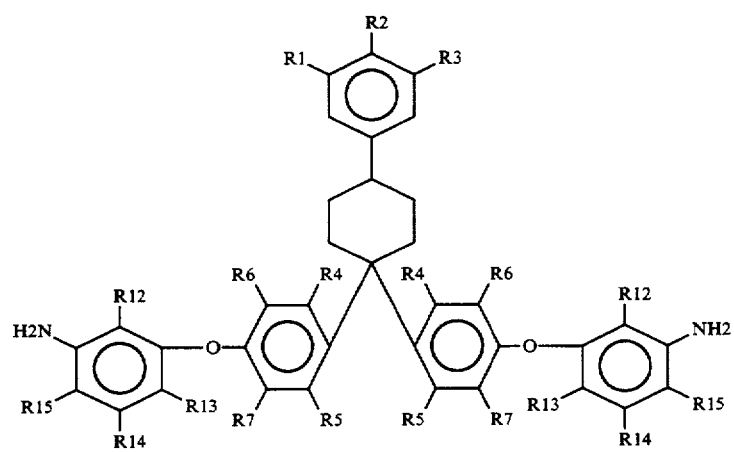

H2N—Z—Si(OR16)3  (7)

wherein R1 to R3 are hydrogen or an alkyl group having 1 to 8 carbon atoms, respectively, and a part or all of them may be the same or different, R4 to R15 are hydrogen, fluorine, trifluoromethyl or an alkyl group having 1 to 3 carbon atoms, respectively, and a part or all of them may be the same or different, and A indicates an aliphatic or aromatic group having a valence of 4.

Z indicates an alkylene group having 2 to 10 carbon atoms or a phenylene group.

R16 is an alkylene group having 1 to 10 carbon atoms.

7) A liquid crystal aligning film obtained by using the polyimide described in 6), wherein the polyimide is obtained by reacting a tetracarboxylic dianhydride represented by the formula (5) and diamino compounds represented by the formula (1) and/or the formula (6) in a solvent, and mixing a silicon compound represented by the formula (7) and reacting the mixture to produce a polyamic acid and heating the resultant polyamic acid.

8) A liquid crystal aligning film obtained by using the polyimide described in 4), wherein the polyimide is a polyether polyimide having as a principal constituent a structure unit represented by the general formula (8):

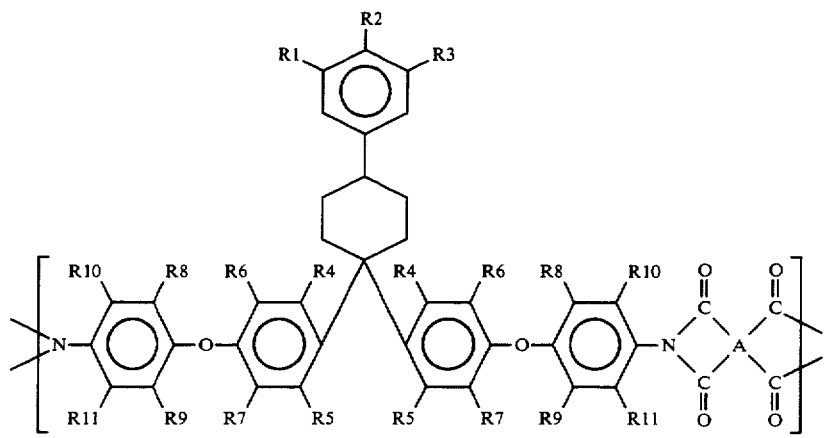

(8)

wherein R1 to R3 are hydrogen or an alkyl group having 1 to 8 carbon atoms, respectively, and a part or all of them may be the same or different, R4 to R11 are hydrogen, fluorine, trifluoromethyl or an alkyl group having 1 to 3 carbon atoms, respectively, and a part or all of them may be the same or different, and A indicates an aliphatic or aromatic group having a valence of 4.

9) A liquid crystal aligning film obtained by using the polyimide described in 8), wherein the polyimide is a polyether polyimide having a substituted imide group represented by the formula (9):

R4 to R11 are hydrogen, fluorine, trifluoromethyl or an alkyl group having 1 to 3 carbon atoms, respectively, and a part or all of them may be the same or different, A indicates an aliphatic or aromatic group having a valence of 4.

Z indicates an alkylene group having 2 to 10 carbon atoms or a phenylene group, and R16 indicates an alkyl group having 1 to 10 carbon atoms.

10) A liquid crystal aligning film obtained by using the polyimide described in 4), wherein the polyimide is a polyether polyimide having as a principal

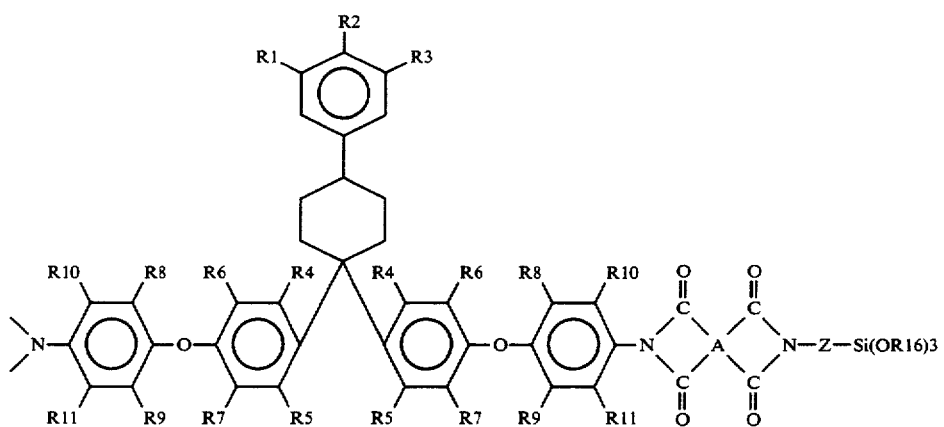

(9)

wherein R1 to R3 are hydrogen or an alkyl group having 1 to 8 carbon atoms, respectively, and a part or all of them may be the same or different, constituent a structure unit represented by the general formula (10):

(10)

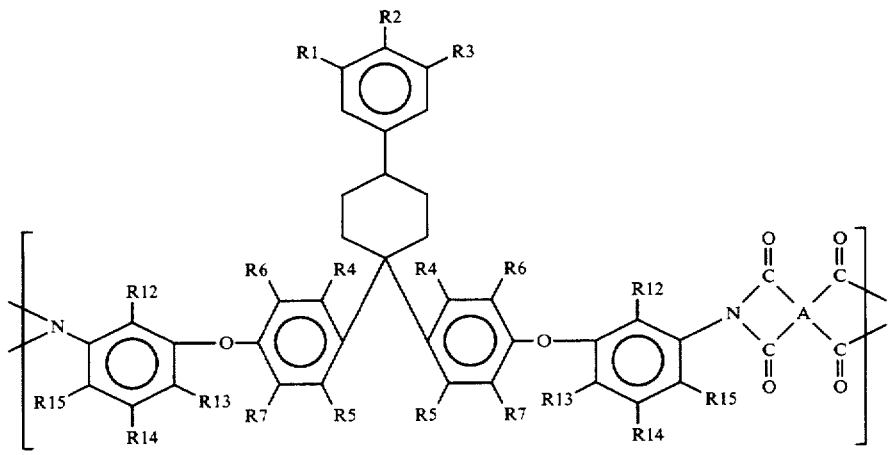

wherein R1 to R3 are hydrogen or an alkyl group having 1 to 8 carbon atoms, respectively, and a part or all of them may be the same or different, R4 to R7 and R12 to R15 are hydrogen, fluorine, trifluoromethyl or an alkyl group having 1 to 3 carbon atoms, respectively, and a part or all of them may be the same or different, A indicates an aliphatic or aromatic group having a valence of 4.

11) A liquid crystal aligning film obtained by using the polyimide described in 10), wherein the polyimide is a polyether polyimide having a structure unit represented by the general formula (11):

(11)

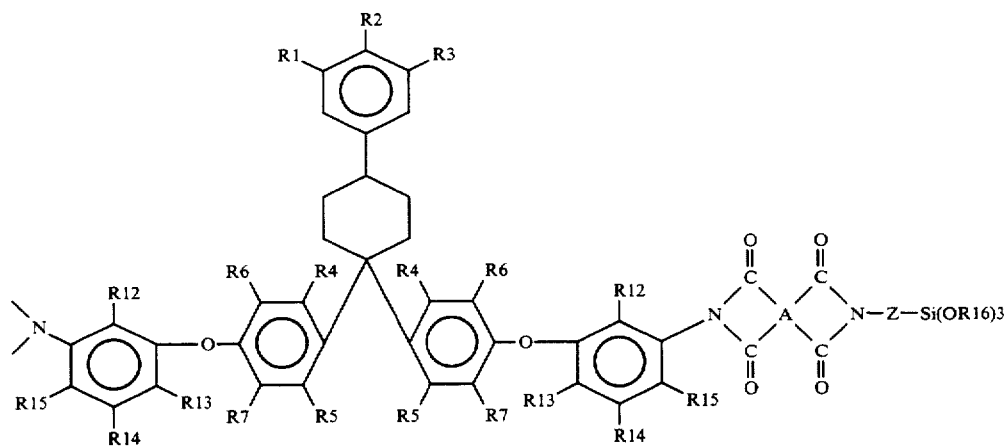

wherein R1 to R3 are hydrogen or an alkyl group having 1 to 8 carbon atoms, respectively, and a part or all of them may be the same or different, R4 to R7 and R12 to R15 are hydrogen, fluorine, trifluoromethyl or an alkyl group having 1 to 3 carbon atoms, respectively, and a part or all of them may be the same or different, A indicates an aliphatic or aromatic group having a valence of 4, Z indicates an alkylene group having 2 to 10 carbon atoms or a phenylene group, and R16 indicates an alkyl group having 1 to 10 carbon atoms.

12) A liquid crystal display device equipping the liquid crystal aligning film as disclosed in any one of the above 4) to 11).

The diamino compounds of the present invention are exemplified by the following compounds.

1,1-bis[4-(4-aminophenoxy)phenyl]-4-phenylcyclohexane,
1,1-bis[4-(4-aminophenoxy)phenyl]-4-(4-methylphenyl)cyclohexane,
1,1-bis[4-(4-aminophenoxy)phenyl]-4-(4-ethylphenyl)cyclohexane,
1,1-bis[4-(4-aminophenoxy)phenyl]-4-(4-n-propylphenyl)cyclohexane,
1,1-bis[4-(4-aminophenoxy)phenyl]-4-(4-n-butylphenyl)cyclohexane,
1,1-bis[4-(4-aminophenoxy)phenyl]-4-(4-n-pentylphenyl)cyclohexane,
1,1-bis[4-(4-aminophenoxy)phenyl]-4-(4-n-hexylphenyl)cyclohexane,
1,1-bis[4-(4-aminophenoxy)phenyl]-4-(4-n-heptylphenyl)cyclohexane,
1,1-bis[4-(4-aminophenoxy)phenyl]-4-(4-n-octylphenyl)cyclohexane, 1,1-bis[4-(4-aminophenoxy)phenyl]-4-(3-methylphenyl)cyclohexane,
1,1-bis[4-(4-aminophenoxy)phenyl]-4-(3-ethylphenyl)cyclohexane,
1,1-bis[4-(4-aminophenoxy)phenyl]-4-(3-n-propylphenyl)cyclohexane,
1,1-bis[4-(4-aminophenoxy)phenyl]-4-(3-n-butylphenyl)cyclohexane,
1,1-bis[4-(4-aminophenoxy)phenyl]-4-(3-n-pentylphenyl)cyclohexane, 1,1-bis[4-(4-aminophenoxy)phenyl]-4-(3-n-hexylphenyl)cyclohexane,
1,1-bis[4-(4-aminophenoxy)phenyl]-4-(3-n-heptylphenyl)cyclohexane,
1,1-bis[4-(4-aminophenoxy)phenyl]-4-(3-n-octylphenyl)cyclohexane,
1,1-bis[4-(2-methyl-4-aminophenoxy)phenyl]-4-phenylcyclohexane,
1,1-bis[4-(2-methyl-4-aminophenoxy)phenyl]-4-(4-methylphenyl)cyclohexane,
1,1-bis[4-(2-methyl-4-aminophenoxy)phenyl]-4-(4-ethylphenyl)cyclohexane,
1,1-bis[4-(2-methyl-4-aminophenoxy)phenyl]-4-(4-n-propylphenyl)cyclohexane,
1,1-bis[4-(2-methyl-4-aminophenoxy)phenyl]-4-(4-n-butylphenyl)cyclohexane,
1,1-bis[4-(2-methyl-4-aminophenoxy)phenyl]-4-(4-n-pentylphenyl)cyclohexane,
1,1-bis[4-(2-methyl-4-aminophenoxy)phenyl]-4-(4-n-hexylphenyl)cyclohexane,
1,1-bis[4-(2-methyl-4-aminophenoxy)phenyl]-4-(4-n-heptylphenyl)cyclohexane,
1,1-bis[4-(2-methyl-4-aminophenoxy)phenyl]-4-(4-n-octylphenyl)cyclohexane,
1,1-bis[3-methyl-4-(4-aminophenoxy)phenyl]-4-phenylcyclohexane,
1,1-bis[3-methyl-4-(4-aminophenoxy)phenyl]-4-(4-methylphenyl)cyclohexane,
1,1-bis[3-methyl-4-(4-aminophenoxy)phenyl]-4-(4-ethylphenyl)cyclohexane,
1,1-bis[3-methyl-4-(4-aminophenoxy)phenyl]-4-(4-n-propylphenyl)cyclohexane,
1,1-bis[3-methyl-4-(4-aminophenoxy)phenyl]-4-(4-n-butylphenyl)cyclohexane,
1,1-bis[3-methyl-4-(4-aminophenoxy)phenyl]-4-(4-n-pentylphenyl)cyclohexane,
1,1-bis[3-methyl-4-(4-aminophenoxy)phenyl]-4-(4-n-hexylphenyl)cyclohexane,
1,1-bis[3-methyl-4-(4-aminophenoxy)phenyl]-4-(4-n-heptylphenyl)cyclohexane,
1,1-bis[3-methyl-4-(4-aminophenoxy)phenyl]-4-(4-n-octylphenyl)cyclohexane,
1,1-bis[4-(2-methyl-4-aminophenoxy)phenyl]-4-(3-methylphenyl)cyclohexane,
1,1-bis[4-(2-methyl-4-aminophenoxy)phenyl]-4-(3-ethylphenyl)cyclohexane,
1,1-bis[4-(2-methyl-4-aminophenoxy)phenyl]-4-(3-n-propylphenyl)cyclohexane,
1,1-bis[4-(2-methyl-4-aminophenoxy)phenyl]-4-(3-n-butylphenyl)cyclohexane,
1,1-bis[4-(2-methyl-4-aminophenoxy)phenyl]-4-(3-n-pentylphenyl)cyclohexane,
1,1-bis[4-(2-methyl-4-aminophenoxy)phenyl]-4-(3-n-hexylphenyl)cyclohexane,
1,1-bis[4-(2-methyl-4-aminophenoxy)phenyl]-4-(3-n-heptylphenyl)cyclohexane,
1,1-bis[4-(2-methyl-4-aminophenoxy)phenyl]-4-(3-n-octylphenyl)cyclohexane,
1,1-bis[3-methyl-4-(2-methyl-4-aminophenoxy)phenyl]-4-phenylcyclohexane,
1,1-bis[3-methyl-4-(2-methyl-4-aminophenoxy)phenyl]-4-(3-methylphenyl)cyclohexane,
1,1-bis[3-methyl-4-(2-methyl-4-aminophenoxy)phenyl]-4-(3-ethylphenyl)cyclohexane,
1,1-bis[3-methyl-4-(2-methyl-4-aminophenoxy)phenyl]-4-(3-n-propylphenyl)cyclohexane,
1,1-bis[3-methyl-4-(2-methyl-4-aminophenoxy)phenyl]-4-(3-n-butylphenyl)cyclohexane,
1,1-bis[3-methyl-4-(2-methyl-4-aminophenoxy)phenyl]-4-(3-n-pentylphenyl)cyclohexane,
1,1-bis[3-methyl-4-(2-methyl-4-aminophenoxy)phenyl]-4-(3-n-hexylphenyl)cyclohexane,
1,1-bis[3-methyl-4-(2-methyl-4-aminophenoxy)phenyl]-4-(3-n-heptylphenyl)cyclohexane,
1,1-bis[3-methyl-4-(2-methyl-4-aminophenoxy)phenyl]-4-(3-n-octylphenyl)cyclohexane,
1,1-bis[4-(2-fluoro-4-aminophenoxy)phenyl]-4-phenylcyclohexane,
1,1-bis[4-(2-fluoro-4-aminophenoxy)phenyl]-4-(4-methylphenyl)cyclohexane,
1,1-bis[4-(2-fluoro-4-aminophenoxy)phenyl]-4-(4-ethylphenyl)cyclohexane,
1,1-bis[4-(2-fluoro-4-aminophenoxy)phenyl]-4-(4-n-propylphenyl)cyclohexane,
1,1-bis[4-(2-fluoro-4-aminophenoxy)phenyl]-4-(4-n-butylphenyl)cyclohexane,
1,1-bis[4-(2-fluoro-4-aminophenoxy)phenyl]-4-(4-n-pentylphenyl)cyclohexane,
1,1-bis[4-(2-fluoro-4-aminophenoxy)phenyl]-4-(4-n-hexylphenyl)cyclohexane,
1,1-bis[4-(2-fluoro-4-aminophenoxy)phenyl]-4-(4-n-heptylphenyl)cyclohexane,
1,1-bis[4-(2-fluoro-4-aminophenoxy)phenyl]-4-(4-n-octylphenyl)cyclohexane,
1,1-bis[4-(2-trifluoromethyl-4-aminophenoxy)phenyl]-4-phenylcyclohexane,
1,1-bis[4-(2-trifluoromethyl-4-aminophenoxy)phenyl]-4-(4-methylphenyl)cyclohexane,
1,1-bis[4-(2-trifluoromethyl-4-aminophenoxy)phenyl]-4-(4-ethylphenyl)cyclohexane,
1,1-bis[4-(2-trifluoromethyl-4-aminophenoxy)phenyl]-4-(4-n-propylphenyl)cyclohexane,
1,1-bis[4-(2-trifluoromethyl-4-aminophenoxy)phenyl]-4-(4-n-butylphenyl)cyclohexane,
1,1-bis[4-(2-trifluoromethyl-4-aminophenoxy)phenyl]-4-(4-n-pentylphenyl)cyclohexane,
1,1-bis[4-(2-trifluoromethyl-4-aminophenoxy)phenyl]-4-(4-n-hexylphenyl)cyclohexane,
1,1-bis[4-(2-trifluoromethyl-4-aminophenoxy)phenyl]-4-(4-n-heptylphenyl)cyclohexane,
1,1-bis[4-(2-trifluoromethyl-4-aminophenoxy)phenyl]-4-(4-n-octylphenyl)cyclohexane,
1,1-bis[3-fluoro-4-(4-aminophenoxy)phenyl]-4-phenylcyclohexane,
1,1-bis[3-fluoro-4-(4-aminophenoxy)phenyl]-4-(4-methylphenyl)cyclohexane,
1,1-bis[3-fluoro-4-(4-aminophenoxy)phenyl]-4-(4-ethylphenyl)cyclohexane,
1,1-bis[3-fluoro-4-(4-aminophenoxy)phenyl]-4-(4-n-propylphenyl)cyclohexane,
1,1-bis[3-fluoro-4-(4-aminophenoxy)phenyl]-4-(4-n-butylphenyl)cyclohexane,
1,1-bis[3-fluoro-4-(4-aminophenoxy)phenyl]-4-(4-n-pentylphenyl)cyclohexane,
1,1-bis[3-fluoro-4-(4-aminophenoxy)phenyl]-4-(4-n-hexylphenyl)cyclohexane,
1,1-bis[3-fluoro-4-(4-aminophenoxy)phenyl]-4-(4-n-heptylphenyl)cyclohexane,
1,1-bis[3-fluoro-4-(4-aminophenoxy)phenyl]-4-(4-n-octylphenyl)cyclohexane,
1,1-bis[3-trifluoromethyl-4-(4-aminophenoxy)phenyl]-4-phenylcyclohexane,
1,1-bis[3-trifluoromethyl-4-(4-aminophenoxy)phenyl]-4-(4-methylphenyl)cyclohexane,
1,1-bis[3-trifluoromethyl-4-(4-aminophenoxy)phenyl]-4-(4-ethylphenyl)cyclohexane, 1,1-bis[3-trifluoromethyl-4-(4-aminophenoxy)phenyl]-4-(4-n-propylphenyl)cyclohexane,
1,1-bis[3-trifluoromethyl-4-(4-aminophenoxy)phenyl]-4-(4-n-butylphenyl)cyclohexane,
1,1-bis[3-trifluoromethyl-4-(4-aminophenoxy)phenyl]-4-(4-n-pentylphenyl)cyclohexane,
1,1-bis[3-trifluoromethyl-4-(4-aminophenoxy)phenyl]-4-(4-n-hexylphenyl)cyclohexane,
1,1-bis[3-trifluoromethyl-4-(4-aminophenoxy)phenyl]-4-(4-n-heptylphenyl)cyclohexane, and
1,1-bis[3-trifluoromethyl-4-(4-aminophenoxy)phenyl]-4-(4-n-octylphenyl)cyclohexane.

The dinitro compounds of the present invention are exemplified by the following compounds.
1,1-bis[4-(4-nitrophenoxy)phenyl]-4-phenylcyclohexane,
1,1-bis[4-(4-nitrophenoxy)phenyl]-4-(4-methylphenyl)cyclohexane,
1,1-bis[4-(4-nitrophenoxy)phenyl]-4-(4-ethylphenyl)cyclohexane,
1,1-bis[4-(4-nitrophenoxy)phenyl]-4-(4-n-propylphenyl)cyclohexane,
1,1-bis[4-(4-nitrophenoxy)phenyl]-4-(4-n-butylphenyl)cyclohexane,
1,1-bis[4-(4-nitrophenoxy)phenyl]-4-(4-n-pentylphenyl)cyclohexane,
1,1-bis[4-(4-nitrophenoxy)phenyl]-4-(4-n-hexylphenyl)cyclohexane,
1,1-bis[4-(4-nitrophenoxy)phenyl]-4-(4-n-heptylphenyl)cyclohexane, and
1,1-bis[4-(4-nitrophenoxy)phenyl]-4-(4-n-octylphenyl)cyclohexane, The diol compounds of the present invention are exemplified by the following compounds.
1,1-bis(4-hydroxyphenyl)-4-phenylcyclohexane,
1,1-bis(4-hydroxyphenyl)-4-(4-methylphenyl)cyclohexane,
1,1-bis(4-hydroxyphenyl)-4-(4-ethylphenyl)cyclohexane,
1,1-bis(4-hydroxyphenyl)-4-(4-n-propylphenyl)cyclohexane,
1,1-bis(4-hydroxyphenyl)-4-(4-n-butylphenyl)cyclohexane,
1,1-bis(4-hydroxyphenyl)-4-(4-n-pentylphenyl)cyclohexane,
1,1-bis(4-hydroxyphenyl)-4-(4-n-hexylphenyl)cyclohexane,
1,1-bis(4-hydroxyphenyl)-4-(4-n-heptylphenyl)cyclohexane, and
1,1-bis(4-hydroxyphenyl)-4-(4-n-octylphenyl)cyclohexane.

Diamino compounds (f) of the present invention are produced by the following reaction process, and diol compounds (c) and dinitro compounds (e) of the present invention are intermediates of the process.

(Step 1)

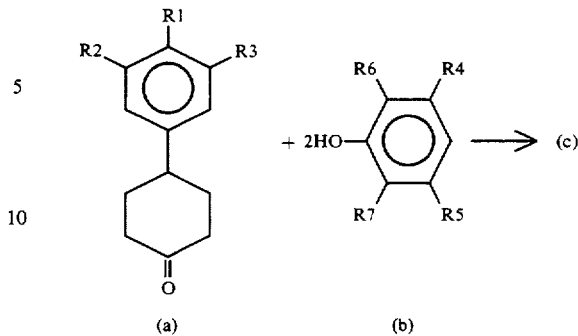

(Step 2)

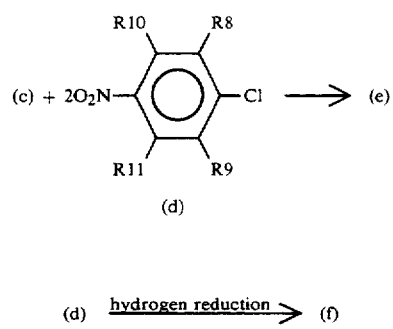

(Step 3)

(d) $\xrightarrow{\text{hydrogen reduction}}$ (f)

In these compounds, R1 to R3 are hydrogen or an alkyl group having 1 to 8 carbon atoms, respectively, and a part or all of them may be the same or different. R4 to R7 or R8 to R11 are hydrogen, fluorine, trifluoromethyl or an alkyl group having 1 to 3 carbon atoms, and a part or all of them may be the same or different.

About the diamino compounds, the production process is summarized as an example.

(1st step)
4-phenylcyclohexanone or its derivative (a) and phenol or the derivative (b) (for example, o-cresol, m-cresol, or 2,6-dimethylphenol) in the absence of solvent or in appropriate solvent (for example, toluene or xylene) are reacted with concentrated hydrochloric acid at a temperature of 0°-70° C. to obtain diol compound (c).

(2nd step)
Diol compound (c) and p-chloronitrobenzene or its derivative (d) (for example, 5-chloro-2-nitrotoluene) in dimethyl sulfoxide (abbreviated as DMSO hereinafter) are condensed with KOH or NaOH at a temperature of 40°-80° C. to obtain dinitro compound (e).

(3rd step)
Dinitro compound (e) in appropriate solvent (for example, toluene, xylene, benzene, ethanol or methanol) is reacted by hydrogen reduction in the presence of palladium-carbon (abbreviated as Pd—C hereinafter) at a temperature of 30°-80° C. to obtain diamino compound (f).

As shown in the reaction process, by appropriate selection of substituting groups R1 to R7 of compounds (a) and (b) in the first step, all kinds of desired diol compounds are obtained, and by appropriate selection of substituting groups R8-R11 of compound (d) in the second step, all kinds of desired dinitro compounds are obtained. Further, in the third step, new diamino compounds of the present invention can be prepared as end products by hydrogen reduction of the dinitro compounds obtained in the second step.

The polyimide-type polymer used for liquid crystal aligning films are usually insoluble in solvents. For providing homogeneous polyimide-type polymer films on a substrate, a precursor polyamic acid is dissolved in a solvent such as N-methyl-2-pyrrolidone (NMP), dimethylacetamide (DMAc), dimethylformamide (DMF), dimethylsulfoxide (DMSO). After the resulting solution is applied on the substrate by a method such as a brush method, a dipping method, a rotation coating method, a spray method, a printing method and the like, the substrate is heated at 100°–450° C., preferably 150°–300° C., and imide-type polymer films are obtained by dehydration and ring closure of the precursor.

The above polyamic acid is prepared by condensation between a tetracarboxylic dianhydride and a diamino compound. The condensation reaction is conducted under anhydrous conditions in a solvent such as N-methyl-2-pyrrolidone (NMP), dimethylacetamide (DMAc), dimethylformamide (DMF), dimethyl sulfoxide (DMSO), dimethyl sulfate, sulfolane, butyrolactone, cresol, phenol, a halogenated phenol, cyclohexanone, dioxane, tetrahydrofuran and the like, preferably N-methyl-2-pyrrolidone (NMP) at temperatures of 50° C. or lower.

Tetracarboxylic dianhydrides are represented by the above formula (5), and include for instance pyromellitic dianhydride, 3, 3', 4, 4'-biphenyltetracarboxylic dianhydride, 2, 2', 3, 3'-biphenyltetracarboxylic dianhydride, 2, 3, 3', 4'-biphenyltetracarboxylic dianhydride, 3, 3', 4, 4'-benzophenonetetracarboxylic dianhydride, 2, 3, 3', 4'-benzophenonetetracarboxylic dianhydride, 2, 2', 3, 3'-benzophenonetetracarboxylic dianhydride, bis(3, 4-dicarboxyphenyl)ether dianhydride, bis(3, 4-dicarboxyphenyl)sulfone dianhydride, 1, 2, 5, 6-naphthalenetetracarboxylic dianhydride and the like. The compounds represented by the following formulas can be exemplified as aliphatic tetracarboxylic dianhydrides.

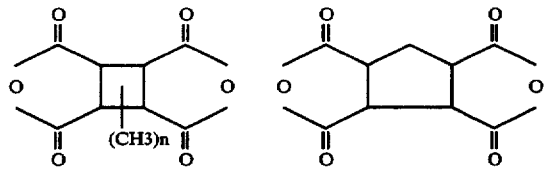

wherein n indicates a real number of 0–4.

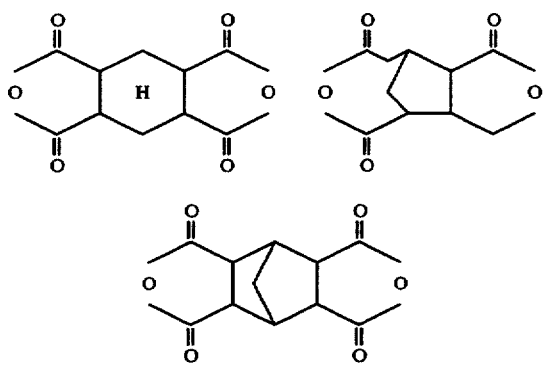

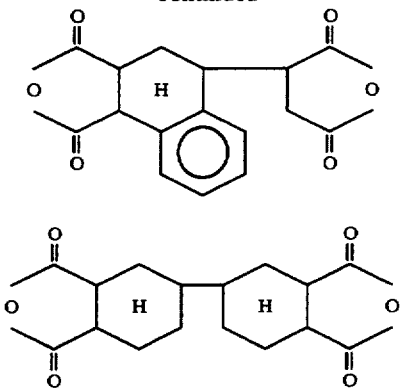

Some of these compounds may contain isomers, and these may be a mixture of the isomers. Further, it is unnecessary to limit the tetracarboxylic dianhydrides used in the present invention to the above cited compounds.

In the liquid crystal aligning film of the present invention, it is possible to increase the adhesivity of the polyimide aligning film on the substrate by adding an aminosilicon compound or a diaminosilicon compound to polyimide.

The aminosilicon compounds represented by the above formula (7) can be exemplified as follows:

3-aminopropyltrimethoxysilane, 3-aminopropyltriethoxysilane, 3-aminopropylmethyldimethoxysilane, 3-aminopropylmethyldiethoxysilane, 3-aminopropyltris(2-methoxyethoxy) silane, 2-aminoethyltrimethoxysilane, 2-aminoethyltriethoxysilane, 2-aminoethylmethyldimethoxysilane, 2-aminoethylmethyldiethoxysilane, 4-aminobutyltrimethoxysilane, 4-aminophenyltrimethoxysilane, 4-aminophenyltriethoxysilane, 4-aminophenylmethyldimethoxysilane, 4-aminophenylmethyldiethoxysilane, 4-aminophenyltris(2-methoxyethoxy) silane, 3-(4-aminophenyl)propyltrimethoxysilane, 3-(4-aminophenyl)propyltriethoxysilane, 3-aminophenyltrimethoxysilane, 3-aminophenyltriethoxysilane, 3-(4-aminophenyl) propylmethyldimethoxysilane, 3-(4-aminophenyl) propylmethyldiethoxysilane, 3-aminophenylmethyldimethoxysilane, and 3-aminophenylmethyldiethoxysilane.

When the aminosilicon compounds are added to the polyimide-type polymers, the content is 50 mol % or less of the polyimide raw materials, preferably 30 mol % or less of the polyimide raw materials, preferably 30 mol % or less.

Further, the diamino compounds are represented by the formula:

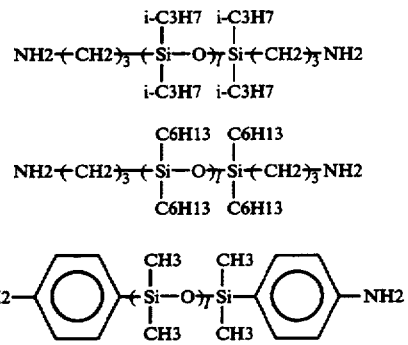

-continued

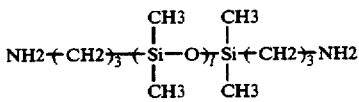

wherein l indicates an integer of 0–4. When these diaminosilicon compounds are added to the polyimide-type polymers, the diaminosilicon compounds can be replaced by 50 mol % or less, preferably 30 mol % or less of the diamino compounds which are polyimide raw materials.

For providing the liquid crystal aligning film of the present invention on a substrate, preferably, a precursor polyamic acid which is obtained by condensation of a tetracarboxylic dianhydride and a diamino compound is applied on the substrate, and the substrate is heated to produce a polyimide-type polymer film on the substrate by dehydration. More concretely, polyamic acid is dissolved in a solvent such as N-methyl-2-pyrrolidone (NMP), dimethylsulfoxide (DMSO), butylcellosolve and ethylcarbitol, the solution is adjusted to 0.1–30% by weight, and the resulting solution is applied on the substrate by a method such as a brush method, a dipping method, a rotation coating method, a spray method, a printing method and the like to form an applied film. Then, the substrate is heated at 100°–450° C., preferably 180°–290° C. to form a polyimide-type polymer film by dehydration and ring closure of the precursor. Before coating with the precursor, the surface of the substrate is treated with a silane coupling agent, and then the polymer film is formed, so that the adhesivity of the polymer film to the substrate can be improved. The obtained film surface is then repeatedly rubbed in the same direction, and a liquid crystal aligning film is obtained.

On the substrate used as a liquid crystal display device, usually electrodes, concretely transparent electrodes of ITO (indium oxide-tin oxide) or tin oxide are formed. Further, an undercoat film such as an insulating film for preventing alkali elution from the substrate, a color filter, color filter overcoat and the like may be prepared between the electrodes and the substrate, and an overcoat film such as an insulating film, a color filter film and the like may be prepared on the electrodes. An active element such as a TFT element, and a nonlinear resistance element may be prepared. The constitution of these electrodes, the undercoat and the like in a liquid crystal cell can be the same as that of conventional liquid crystal display devices.

Using the substrate prepared by the above process, a liquid crystal display device is prepared by forming a cell, injecting a liquid crystal into the cell and sealing the cell. As the enclosure of the liquid crystal, conventional nematic liquid crystals, or several kinds of liquid crystals such as a liquid crystal adding a bicolor pigment can be used.

The liquid crystal aligning films of the present invention are characterized in that uniform and high pretilt angles can be realized over the whole display surface of the substrates by the conventional rubbing treatment.

The liquid crystal display devices of the present invention are characterized in that they have liquid crystal aligning films having characteristics that can realize uniform and high pretilt angles over the whole display surface of the wide substrates by the conventional rubbing treatment, and the liquid crystal aligning films, namely above-mentioned films of the present invention.

The devices are generally constituted from substrates, a voltage application means, liquid crystal aligning films, liquid crystal layers and the like.

DESCRIPTION OF PREFERRED EMBODIMENTS

The following examples illustrate the present invention more specifically, but the present invention is not limited to these examples.

Figure 3:
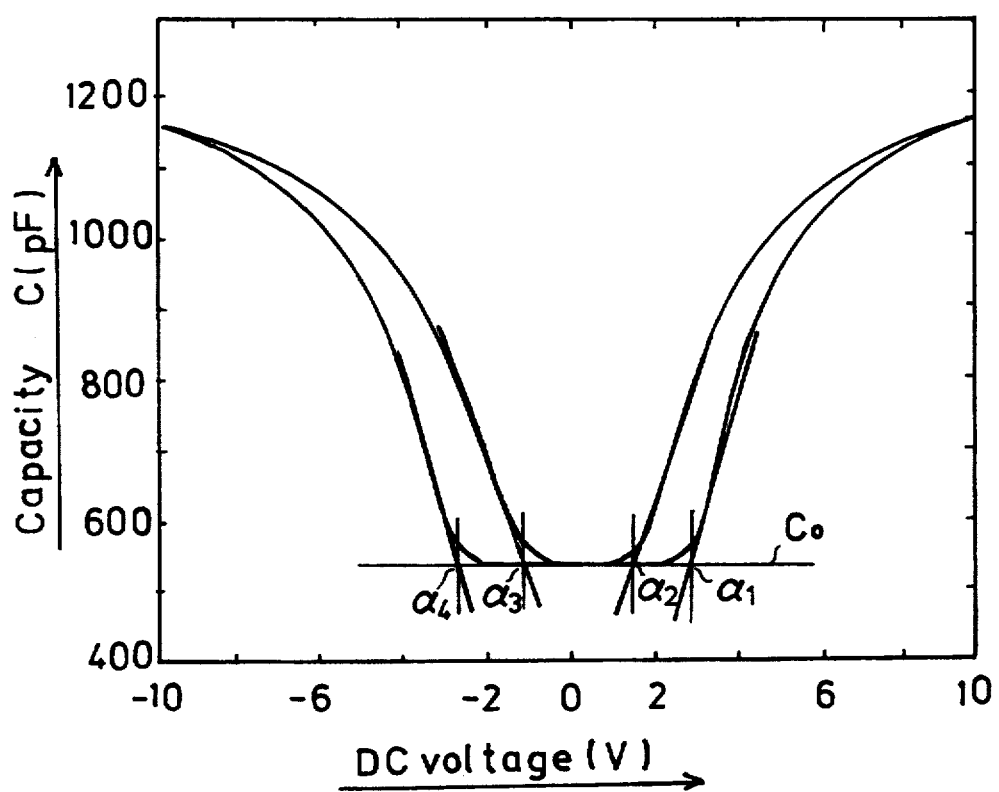
FIG. 3 is a graph showing C–V hysteresis curves.

In each example and comparative example, the afterimage degrees were determined by using a C–V curve method. The C–V curve method was conducted by applying an alternating current of 25 mV and 1 kHz to a crystal cell and ing a triangle wave (abbreviated as DC voltage hereinafter) of a frequency of 0.036 Hz, sweeping the DC voltage within the limits of $-10$ V to 10 V and recording the change of capacity C. When the voltage is swept to a positive side (0→10 V), the capacity becomes high. Then, the voltage is swept to a negative side (0→$-10$ V), and the capacity becomes low. In the same manner, when the voltage is swept to a side more negative than 0 (10→0 V), the capacity becomes high. The voltage is swept to a positive side ($-10$→0 V), and the capacity becomes low. After repeating several cycles, the wave forms obtained are as shown in FIG. 3. When the electric charge differences formed on the aligning film surface are stabilized, the voltage curves are hysteresis curves at the positive side and the negative side as shown in FIG. 3. On the basis of FIG. 3, a residual electric charge is determined by drawing tangent lines to each C–V curve, drawing a line of capacity ($C_0$) at 0 of the DC voltage, seeking each intersecting point ($\alpha_1$–$\alpha_4$) of the tangent lines and the line of capacity ($C_0$), calculating the voltage differences of each two points at the positive side $|\alpha_1$–$\alpha_2|$ and at the negative side $|\alpha_3$–$\alpha_4|$, and then calculating the average voltage difference, namely $(|\alpha_1$–$\alpha_2|+|\alpha_3$–$\alpha_4|)/2$. When the film thickness of the liquid crystal cell and the film thickness of the aligning film are the same, the residual electric charge can be used as a parameter of the electric charge displacement and the stability. Namely, when aligning films having smaller remaining electric charge are used, the afterimage phenomenon of the liquid crystal display device can be reduced.

EXAMPLE 1

<Synthesis of diamino compounds>
(1st step):

To a mixture of 51.6 g of 4-phenylcyclohexane, 111.5 g of phenol and 65.7 g of calcium chloride, 24.7 ml of concentrated hydrochloric acid was slowly added dropwise by vigorous stirring of the mixture at room temperature. Then, the mixture was stirred for eight hours and left for more than 168 hours at room temperature. 0.3 liters of warm water and one liter of ethyl acetate were added to the mixture to dissolve by heating, and the mixture was washed with a saturated sodium chloride solution (warm water of 40°–50° C. was used). After drying with MgSO$_4$, the mixture was filtered and concentrated. The resultant concentrate was recrystallized with toluene to obtain 64.9 g of white 1,1-bis(4-hydroxyphenyl)-4-phenylcyclohexane. The melting point was 262.1°–263.3° C.

(2nd step):

A mixture of 30.0 g of 1,1-bis(4-hydroxyphenyl)-4-phenylcyclohexane obtained in the first step, 200 ml of DMSO and 12.7 g of KOH was dissolved by heating at 65° C. with stirring. 26.1 g of p-chloronitrobenzene dissolved in 50 ml of DMSO was added dropwise at 65° C. to the mixture, and the reaction mixture was aged for nine hours. After the reaction finished, the reaction mixture was cooled to room temperature and extracted with dichloromethane, and the organic phase was washed with a 1N-HCl water solution. Then, the organic phase was washed with a 1N-NaOH aqueous solution and then a saturated sodium chloride water solution until the washed water became neutral, dried over $MgSO_4$, and treated with an alumina column. The organic solvent of the eluted solution was distilled away.

The resulting concentrates were recrystallized from toluene to obtain 41.6 g of pale yellow 1,1-bis[4-(4-nitrophenoxy)phenyl]-4-phenylcyclohexane crystals. The melting point was 215.9°–217.6° C.

(3rd step):

After 41.0 g of 1,1-bis[4-(4-nitrophenoxy)phenyl]-4-phenylcyclohexane obtained by the second step was dissolved in mixed solvent of 300 ml of toluene and 80 ml of solmix, 3.0 g of Pd-C catalyst (5% quality, 55.9% moisture content) was added to the solution. The mixture was cooled with water and contacted with hydrogen gas at atmospheric pressure with stirring. After the hydrogen absorption was finished, the catalyst was filtered out and the solution was concentrated. The concentrates were recrystallized from toluene to obtain 26.5 g of 1,1-bis[4-(4-aminophenoxy)phenyl]-4-phenylcyclohexane of the diamino compound of the present invention. The melting point was 90.7°–92.2° C.

Figure 1:
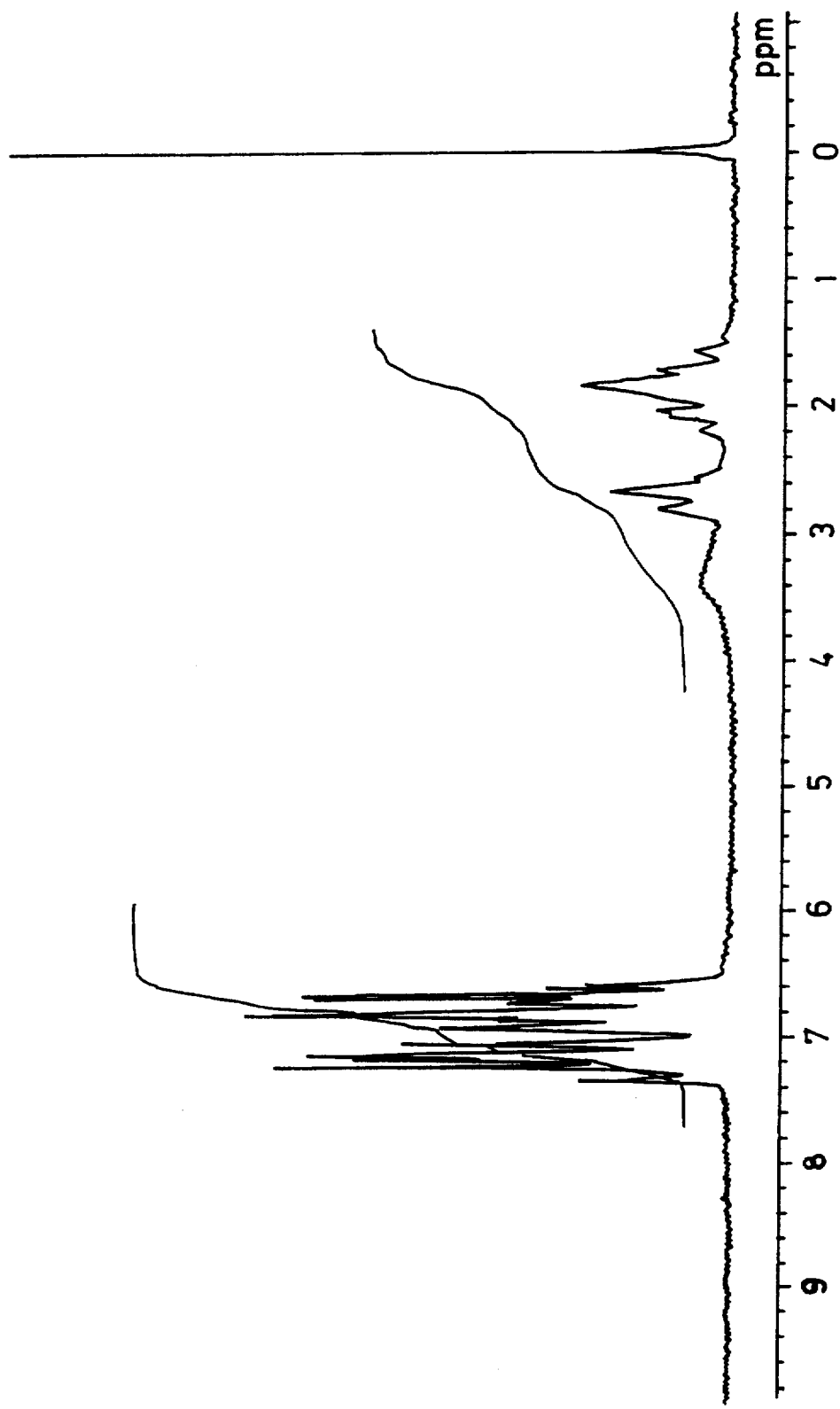
FIG. 1 is a $^1$H-NMR spectrum chart of the diamino compound obtained in Example 1.

The proton nuclear magnetic resonance spectrum ($^1$H-NMR) of the compound is shown in FIG. 1.

<Production of liquid crystal aligning films>

To a three-necked flask equipped with a stirrer, a thermometer, a condenser and a nitrogen displace apparatus, 12.91 g of 1,1-bis[4-(4-aminophenoxy)phenyl]-4-phenylcyclohexane and 165.00 g of N-methyl-2-pyrrolidone were charged, and the mixture was dissolved with stirring. Then, the mixture was cooled to 10° C., 6.11 g of pyromellitic dianhydride was added, and the mixture was reacted with stirring. After one hour, 1.35 g of paraaminophenyltrimethoxysilane was added, and the mixture was reacted with stirring at 15° C. Then, the reaction solution was diluted with 18.33 g of butyl Cellosolve to obtain a solution of polyamic acid (10% by weight, $\eta_{20}$=120 cps).

After the solution was diluted with twice by volume of N-methyl-2-pyrrolidone and twice by volume of butyl Cellosolve, the solution was applied by a rotation coating method (a Spinner method) on glass substrates equipped with transparent electrodes at the one side. The coating conditions were 2000 rpm and 20 seconds. After coating, the substrates were preheated at 10° C. for 10 minutes and heated at 200° C. for one hour to obtain polyimide films having film thickness of 60 nm on the substrates.

Then, the film surface of two pieces of the substrates was rubbed, respectively. A liquid crystal cell having thickness of about 20 μm was assembled by the substrates so as to be oriented in parallel and anti parallel rubbing directions. Liquid crystal ZLI-1132 manufactured by Merck Company was kept in the liquid crystal cell. Then, the liquid crystal was treated with heating at 130° C. for 30 minutes. The aligning properties of the obtained liquid crystal display device was excellent, and the pretilt angle was 5 degrees by a crystal rotation method. By the same method, a liquid crystal cell having thickness of 6 μm was assembled and the residual electric charge determined was 0.02 V at 25° C.

Then, by the same method as described in the above, polyimide films were obtained on glass substrates equipped ITO transparent substrates at 640×200 dots, the film surface was rubbed to obtain a twist of 240 degrees, a cell was assembled by the substrates, liquid crystal LIXON-4011 (manufactured by CHISSO CORPORATION) was injected into the cell, and a liquid crystal display device was obtained. It was found that the liquid crystal display device has excellent properties without domain and afterimage phenomenons by the driving test.

EXAMPLE 2 <Synethesis of diamino compounds>

Conditions of operation were the same as described in Example 1, except that 4-phenylcyclohexanone was changed to 4-(4-ethylphenyl)cyclohexanone.

In the first step, 1,1-bis(4-hydroxyphenyl)-4-(4-ethylphenyl)cyclohexane of white crystals was obtained. The melting point was 187.3°–187.7° C.

In the second step, 1,1-bis[4-(4-nitrophenoxy)phenyl]-4-(4-ethylphenyl)cyclohexane of pale yellow crystals was obtained. The melting point was 204.5°–205.0° C.

In the third step, 1,1-bis[4-(4-aminophenoxy)phenyl]-4-(4-ethylphenyl)cyclohexane was obtained. The compound was pale brown liquid at room temperature.

Figure 2:
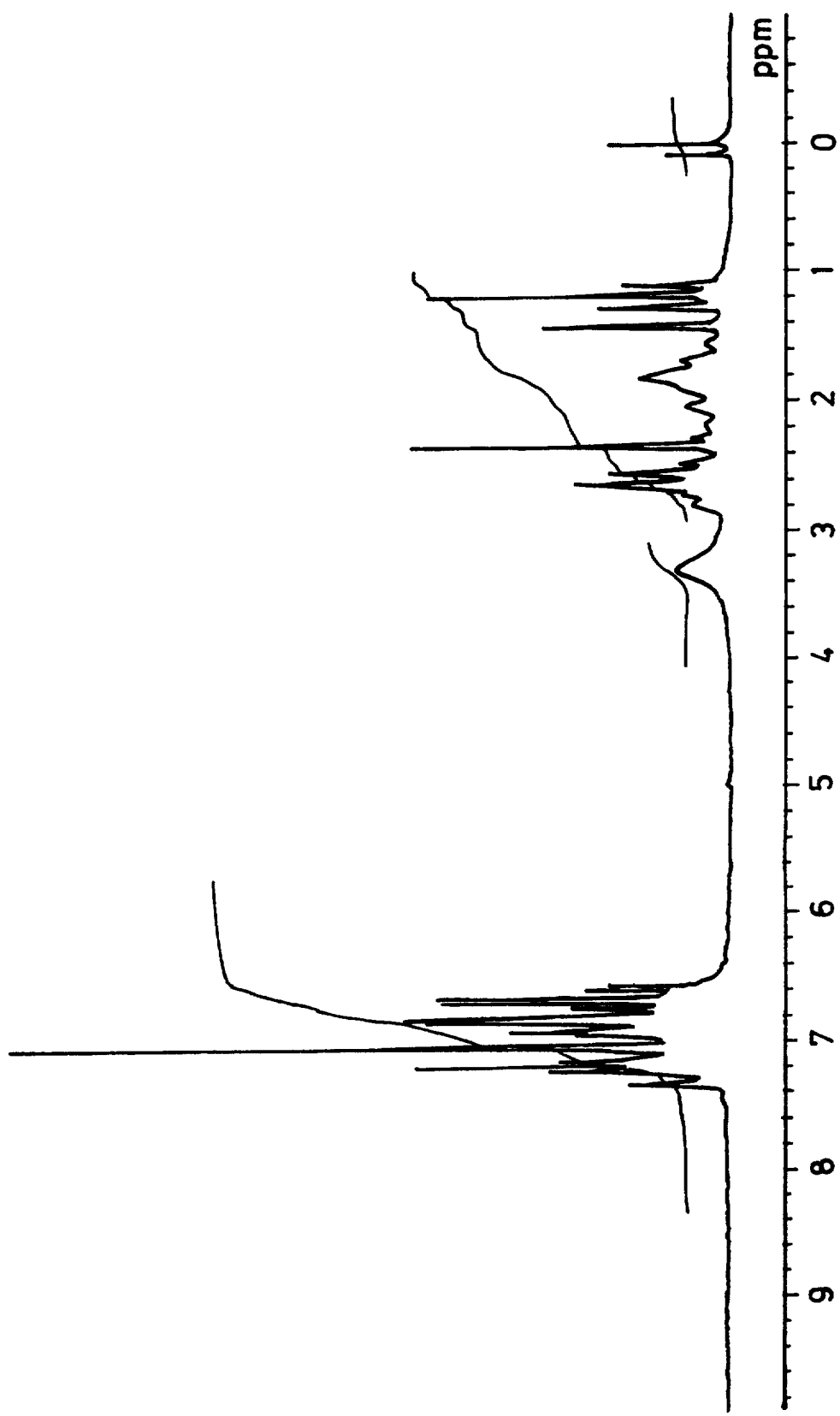
FIG. 2 is a $^1$H-NMR spectrum chart of the diamino com pound obtained in Example 2.

The chart of $^1$H-NMR of the compound is shown in FIG. 2.

<Production of liquid crystal aligning films>

Under the same conditions as in Example 1 except that 1,1-bis[4-(4-aminophenoxy)phenyl]-4-phenylcyclohexane was changed to 1,1-bis[4-(4-aminophenoxy)phenyl]-4-(4-ethylphenyl)cyclohexane, 10% by weight of a polyamic acid solution having a viscosity of 120 cps was obtained.

The liquid crystal aligning properties of the liquid crystal display device obtained by using the above solution under the same conditions as in Example 1 were excellent, and the pretilt angle was six degrees. Using the same method as in Example 1, a liquid crystal cell having a cell thickness of 6 μm was assembled, and the residual charge determined was 0.02 V at 25° C.

Further, the liquid crystal display device obtained has excellent properties without domain and afterimage phenomenons by the same driving test as in Example 1.

COMPARATIVE EXAMPLE 1

<Production of liquid crystal aligning films>

A polyamic acid solution (10% by weight, $\eta_{20}$=113 cps) was obtained from a diamino compound of 2,2-bis[4-(4-aminophenoxy)phenyl]propane by using the same operation as in Example 1.

The pretilt angle of the liquid crystal display devices, which was obtained by using the above solution under the same conditions as in Example 1, was three degrees. Crystal liquid cell having a cell thickness of 6 μm was assembled by using the same method as in Example 1, and the residual charge determined was 0.30 V at 25° C.

Further, by the driving test as shown in Example 1, domain and afterimage phenomenons were found.

As a result, it is clear that the liquid crystal aligning films obtained by using 1,1-bis[4-(4-aminophenoxy)-phenyl]-4-(4-alkylphenyl)cyclohexane as raw material have uniform and high pretilt angles over the whole display surface of the wide substrates and the liquid crystal display devices obtained by using the aligning films have excellent quality without domain and afterimage phenomenons. Moreover, when the chain length of alkyl bonded to phenylcyclohexane in the raw material is elongated, the pretilt angle of the films can be widen. When the chain length is suitably selected, the most suitable pretilt angle required in the production of liquid crystal display devices can be obtained.

The present invention has merits as follows. The diamino compounds, and the dinitro compounds and the diol compounds that are intermediates of the diamino compounds of the present invention are new compounds. The polyimide compounds obtained by using the diamino compounds as raw materials have excellent properties as liquid crystal aligning films. For example, the polyimide compounds can be changed into liquid crystal aligning films having uniform and high pretilt angles over the whole display surface of the wide substrates, which are required to STN liquid crystal display devices by conventional rubbing treatment. Further, the liquid crystal display devices using the liquid crystal aligning films have excellent quality without domain and afterimage phenomenons. It is considered that these effects are brought by a phenylcyclohexane ring and an alkyl group bonded to the ring of the diamino compounds of the raw materials. The diamino compounds of the present invention having the above characteristics are designed as raw materials of liquid crystal aligning films for STN. Further, these compounds can be used for the other polymer compounds such a polyimides and polyamides and their property modification. It is expected to use for the other epoxy cross-linking materials or to introduce new characteristic properties into polymer compounds.

We claim:

1. A dinitro compound represented by a general formula (2):

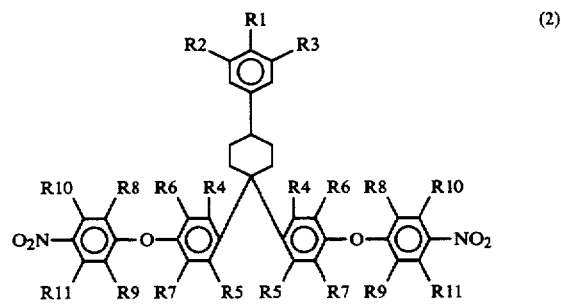

wherein R1 to R3 are hydrogen or an alkyl group having 1 to 8 carbon atoms, respectively, and a part or all of them may be the same or different, R4 to R11 are hydrogen, fluorine, trifluoromethyl or an alkyl group having 1 to 3 carbon atoms, respectively, and a part or all of them may be the same or different.

* * * * *